Figure 1:
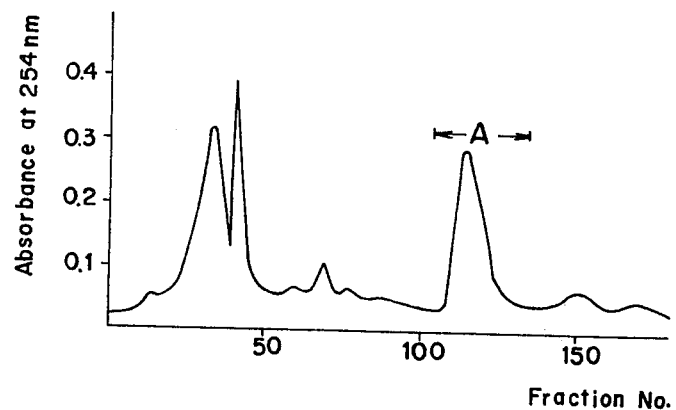

United States Patent [19]

Tanaka et al.

[11] Patent Number: 4,465,673

[45] Date of Patent: Aug. 14, 1984

[54] PENTAGALLOYLGLUCOSE ANTIVIRAL COMPOSITION

[75] Inventors: Yasuo Tanaka, 5-103-6, Midorigaoka, Yao-shi, Osaka-fu, Japan; Masayuki Takechi, Nara, Japan

[73] Assignees: Yasuo Tanaka, Yao; Gakko Jojin Kinki Daigaku (Educational Foundation Kinki of University), Higashiosaka, both of Japan

[21] Appl. No.: 456,781

[22] Filed: Jan. 10, 1983

[51] Int. Cl.$^3$ .............................................. A61K 31/70
[52] U.S. Cl. .................................. 424/180; 536/18.1; 536/18.2; 536/119
[58] Field of Search .............. 424/180; 536/18.1, 18.2, 536/119

[56] References Cited

U.S. PATENT DOCUMENTS 4,107,425  8/1978  Pfeffer et al. ...................... 536/18.2

FOREIGN PATENT DOCUMENTS 92298  7/1981  Japan ................................. 536/18.2
118096  9/1981  Japan ................................. 536/18.2

OTHER PUBLICATIONS

Nishizawa et al., "Chem. Pharm. Bull.", vol. 28, No. 9, 1980, pp. 2850–2852.

*Primary Examiner*—Johnnie R. Brown
*Attorney, Agent, or Firm*—Wegner & Bretschneider

[57] ABSTRACT

A composition comprising 1,2,3,4,6-pentagalloyl-glucose is useful as an antiviral agent.

5 Claims, 2 Drawing Figures

PENTAGALLOYLGLUCOSE ANTIVIRAL COMPOSITION

The present invention relates to an agent for prophylactic or therapeutic treatment of virus diseases.

There have been a great delay in the development of the medicine for virus diseases as compared with that for bacterial diseases. Although some of chemically synthesized substances have a significant antiviral activity, they cannot be used for antiviral agent due to their considerable toxicity or side-effect.

It has therefore been strongly demanded to develop an antiviral agent which is effective and less toxic.

The inventors of the present invention have taken note of the fact that the crude drugs or the Chinese herbal remedies are generally less toxic, and have searched for the antiviral substance in crude drugs or the Chinese herbal remedies. As a result of an extensive study, it has now been discovered that 1,2,3,4,6-pentagalloylglucose, which is contained in peony root bark (Moutan Cortex), peony root (Paeoniae Radix) etc., has an excellent antiviral activity.

In one aspect of the present invention, there is provided a pharmaceutical composition useful as an antiviral agent comprising a therapeutically effective amount of 1,2,3,4,6-pentagalloylglucose in admixture with a pharmaceutically acceptable excipient.

In another aspect of the present invention, there is provided a method for treating virus disease, such as herpes simplex, in mammals which method comprises administering to a subject in need of such treatment a therapeutically effective amount of, or a pharmaceutical composition containing a therapeutically effective amount of, 1,2,3,4,6-pentagalloylglucose.

The compound 1,2,3,4,6-pentagalloylglucose have the following formula:

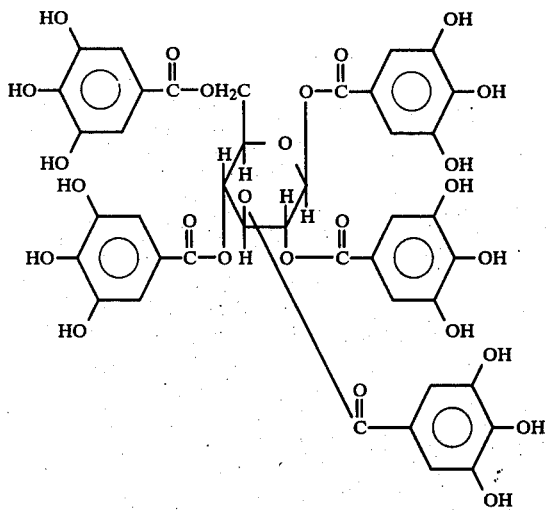

It is a known compound and had been isolated from peony root (Paeoniae Radix) by Nishioka et al. (Chem. Pharm. Bull. (Tokyo), 28, 2850, 1980).

The said compound 1,2,3,4,6-pentagalloylglucose may be obtained by extracting peony root bark (Moutan Cortex), peony root (Paeoniae Radix), nutgalls (Galla halepensis), Chinese nutgalls (Galla Rhois) etc. as the crude drug or the Chinese herbal remedies, or corresponding parts of green or dried peony plants (*Paeonia suffruticosa* and *Paeonia albiflora*), with a hydrophilic organic solvent such as methanol, ethanol, acetone etc. or a mixture of these solvent with water, and purifying the extract by taking advantage of the difference in solubility to various solvents and/or difference in affinity to various adsorbents etc.

The obtained 1,2,3,4,6-pentagalloylglucose exhibits an excellent antiviral activity to a variety of pathogenic viruses and therefore useful in prophylactic and therapeutic treatment of virus diseases including herpes simplex, chickenpox, verruca etc.

For prophylactic and/or therapeutic administration, the antiviral agent according to the invention is used in the form of conventional pharmaceutical preparation including composition for oral, parenteral or, more preferably, external administration. The composition for external administration may be an ointment (oily ointment or hydrophilic ointment), cream, lotion, liniment etc. These compositions contain 1,2,3,4,6-pentagalloylglucose, as an active ingredient, in admixture with pharmaceutically acceptable carriers such as liquid paraffin, Isopar, vaseline, silicone oil, higher aliphatic alcohols (e.g. palmityl alcohol, oleyl alcohol etc.), higher fatty acids (e.g. myristic acid, stearic acid etc.), fatty acid esters (e.g. microcrystalline wax, isopropyl myristate etc.), lanolin, Plastibase (a mixture of liquid paraffin and polyethylene), polyethylene glycol, water etc. If needed, there may be included, in the above preparations, emulsifying agents (e.g. fatty acid monoglyceride, sorbitan fatty acid ester, polyoxyethylene lauryl ether etc.), wetting agents (glycerin, propylene glycol, sorbit etc.), preservatives (methyl or propyl p-hydroxybenzoate etc.), antioxidants (BHA etc.), pH-adjusters (citric acid etc.), suspending agents (CMC etc.) and other drugs (e.g. antipruritic, analgesic etc.). The composition for external administration may be endermatic. The composition for oral or parenteral administration, including injectable composition, may be prepared by conventional method.

While the dosage of the active ingredient, i.e. 1,2,3,4,6-pentagalloylglucose, may vary from and also depend upon a kind of preparation, age of the patient and conditions of the affected part, an average concentration of 0.001–0.5%, preferably 0.01–0.1%, of the active ingredient is sufficient for composition for external administration.

Following Examples are given only for explanation of the invention in more detail. In Examples 4 through 9, the active ingredient is 1,2,3,4,6-pentagalloylglucose.

EXAMPLE 1

Peony root bark (root bark of *Paeonia suffruticosa*, 50 g) was extracted by immersing in menthanol (500 ml) for a week. The extract was concentrated to dryness and the residue was extracted with ether and water. The aqueous layer was extracted with ethyl acetate. The ethyl acetate layer was concentrated. The residue was lyophilized, applied to a Sephadex LH-20 column equilibrated with methanol and eluted with methanol at a flow rate of 30 ml/hour. The eluate was divided into 20 ml fractions, and 50 μl of each fraction was diluted with 2.5 ml of methanol and the absorbance at 254 nm was determined to give the result shown in FIG. 1. Fractions corresponding to a part indicated by A in FIG. 1 were collected, concentrated and lyophilized to give crude 1,2,3,4,6-pentagalloylglucose.

EXAMPLE 2

Figure 2:
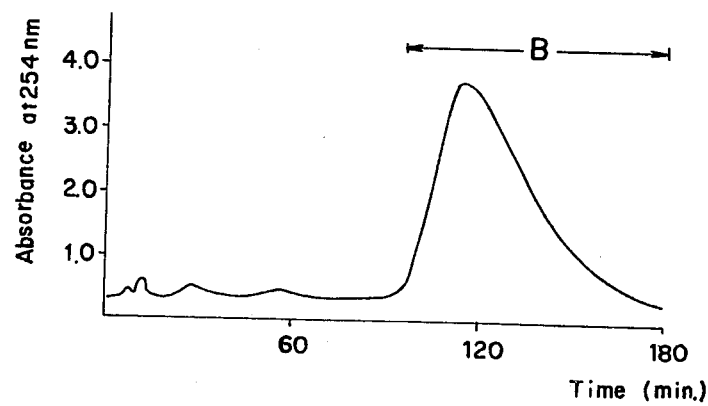

The crude 1,2,3,4,6-pentagalloylglucose obtained in Example 1 was dissolved in 25% methanol (20 ml). A portion (5 ml) of the solution was applied to a Lichroprep RP-18 column (0.8×200 cm) and eluted with 25% methanol at a flow rate of 5 ml/min. The absorbance at 254 nm of the eluate was determined to give the result shown in FIG. 2. Fractions corresponding to a part indicated by B in FIG. 2 were collected. The chromatography was repeated four times. The collected fractions were combined, concentrated and lyophilized to give purified 1,2,3,4,6-pentagalloylglucose, which was homogenous on three different paper chromatographies and high performance liquid chromatography, and identical in NMR spectrum with the authentic sample.

EXAMPLE 3

Examples 1 and 2 were substantially repeated except that the peony root bark is replaced with peony root (roots of Paeonia albiflora, 100 g) to give purified 1,2,3,4,6-pentagalloylglucose.

EXAMPLE 4

| | | Amount (g) |
|---|---|---|
| (A) | Active ingredient | 0.05 |
| | Isopropyl myristate | 5 |
| (B) | Plastibase | 94.95 |

An oily ointment was prepared by gradually adding premixed two ingredients in (A) to (B), and thoroughly mixing them.

EXAMPLE 5

| | | Amount (g) |
|---|---|---|
| (A) | Active ingredient | 0.05 |
| | Isopropyl myristate | 5.95 |
| (B) | Isopropyl myristate | 10 |
| | Vaseline | 66 |
| | Liquid paraffin | 5 |
| | Microcrystalline wax | 13 |

An oily ointment was prepared by adding premixed (A) to (B) in melted state at 45°–50° C., and stirring until the mixture was solidified.

EXAMPLE 6

| | | Amount (g) |
|---|---|---|
| (A) | Active ingredient | 0.05 |
| | Polyethylene glycol (400) | 11.95 |
| (B) | Polyethylene glycol (400) | 12 |
| | Polyethylene glycol (4000) | 76 |

A hydrophilic ointment was prepared by adding premixed (A) to (B) which is previously melted at 70° C. and cooled to 50° C., and stirring until the mixture was solidified. The hydrophilic ointment may further include Carbopol 934.

EXAMPLE 7

| | | Amount (g) |
|---|---|---|
| (A) | Active ingredient | 0.01 |
| | Isopropyl myristate | 5.99 |
| | Stearic acid | 19 |
| | Cethl alcohol | 4 |
| (B) | Polyoxyethylene lauryl ether | 2 |
| | Glycerin monostearate | 0.5 |
| | Propylene glycol | 4 |
| | Citric acid | 0.05 |
| (C) | Distilled water | 64.35 |
| | Methyl p-hydroxybenzoate | 0.05 |
| | p-Hydroxybenzoic acid | 0.05 |

A cream was prepared by adding (C) which is melted at 85° C. to (B) which is melted at 80° C., further adding melted (A) to the mixture at 55° C., and stirring thoroughly.

EXAMPLE 8

| | | Amount (g) |
|---|---|---|
| (A) | Active ingredient | 0.001 |
| | Propylene glycol | 12 |
| | Polyoxyethylene lauryl ether | 1 |
| | Isosteraric acid | 1 |
| | Octyldodecanol | 4 |
| | Citric acid | 0.075 |
| (B) | Distilled water | 78.924 |

A lotion was prepared by adding (B) to (A) which is melted at 40° C.

EXAMPLE 9

| | | Amount (g) |
|---|---|---|
| (A) | Active ingredient | 0.05 |
| | Acetyl hydrocortisone | 0.5 |
| | Diphenhydramine | 0.5 |
| | White vaseline | 4.85 |
| (B) | White vaseline | 95 |

An ointment was prepared by mixing (B) with melted (A).

EXAMPLE 10

Antiviral activity of 1,2,3,4,6-pentagalloylglucose against herpes simplex virus was assayed. Procedure:

Monolayers were prepared from dispersed FL cells in Petri dishes of diameter 35 mm, 24 hours prior to the assay. On carrying out the assay, the medium in each dish was poured off and each dish received 1 ml of medium containing herpes simplex virus. The dishes were incubated at 36° C. in a humidified atmosphere containing 5% of gaseous carbon dioxide. After an hour, each dish further received 1 ml of medium and 20–200 μl of an aqueous 1,2,3,4,6-pentagalloylglucose solution. Incubation was continued for 24 hours and then all the dishes were inspected for multinucleated giant cell. Antiviral activity was defined as the minimum concentration of sample at which no multinucleated giant cell appeared. The results obtained are as follows:

| Sample | Antiviral activity (μg/ml) |
|---|---|
| Product of Example 1 | 26 |
| Product of Example 2 | 25 |

Acute toxicity of 1,2,3,4 6-pentagalloylglucose was assayed using rats in a usual manner. It was found that the toxicity was extremely low.

What is claimed is:

1. An antiviral composition comprising an amount of 1,2,3,4 6-pentagalloylglucose effective against herpes simplex virus in admixture with a pharmaceutically acceptable excipient.

2. The pharmaceutical composition of claim 1 in which 1,2,3,4 6-pentagalloylglucose is extracted from peony root.

3. The pharmaceutical composition of claim 1 in which 1,2,3,4,6-pentagalloylglucose is extracted from peony root bark.

4. A method for treating herpes simplex virus disease in mammals which method comprises administering to a subject in need of such treatment a therapeutically effective amount of, or a pharmaceutical composition containing a therapeutically effective amount of, 1,2,3,4,6-pentagalloylglucose.

5. The method of claim 4 in which the virus disease is caused by an infection of herpes simplex virus.

* * * * *